United States Patent [19]

Reeves et al.

[11] Patent Number: 4,641,531

[45] Date of Patent: Feb. 10, 1987

[54] ULTRASONIC INSPECTION APPARATUS AND METHOD FOR LOCATING MULTIPLE DEFECTS IN ECCENTRIC WALL TUBULAR GOODS

[76] Inventors: Roger D. Reeves, 821 Pinegrove, Longview, Tex. 75604; Dale F. Hawkey, #8-205-Chatelain Drive, St. Albert, Canada

[21] Appl. No.: 844,513

[22] Filed: Mar. 27, 1986

[51] Int. Cl.⁴ .............................................. G01N 29/04
[52] U.S. Cl. ...................................... 73/622; 73/637; 73/642; 73/628
[58] Field of Search ................. 73/622, 633, 637, 638, 73/642, 628

[56] References Cited

U.S. PATENT DOCUMENTS

| | | | |
|---|---|---|---|
| 4,404,853 | 9/1983 | Livingston | 73/622 |
| 4,475,399 | 10/1984 | Livingston | 73/622 |
| 4,487,072 | 12/1984 | Livingston | 73/622 |
| 4,523,468 | 6/1985 | Derkacs et al. | 73/622 |
| 4,541,064 | 9/1985 | Livingston | 73/637 |
| 4,559,825 | 12/1985 | Martens | 73/622 |

*Primary Examiner*—Howard A. Birmiel
*Attorney, Agent, or Firm*—Charles D. Gunter, Jr.

[57] ABSTRACT

An ultrasonic inspection apparatus is shown for locating multiple defects in eccentric wall tubing or goods. A plurality of transducers are arranged in mated pairs, each of the pairs including a sender element for transmitting an ultrasonic shear wave and a receiver element for receiving a reflected ultrasonic wave component from the tubular goods being inspected. Each sender element is a point focus transducer having sufficiently high resolution to maintained detectability of defects in the tubular goods. Each receiver element is a wide focal width transducer having a large effective beam width area to compensate for eccentricity in the wall of the tubular goods.

10 Claims, 13 Drawing Figures

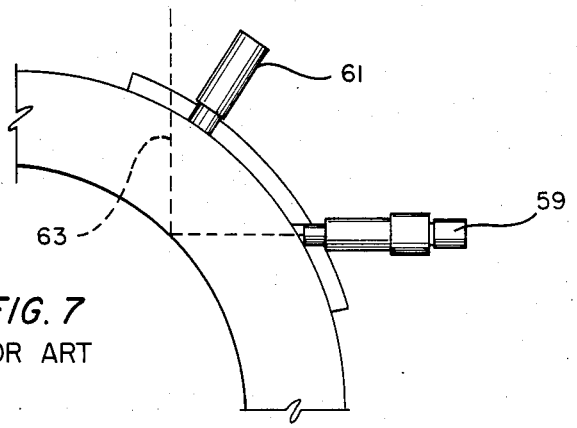
FIG. 7
PRIOR ART
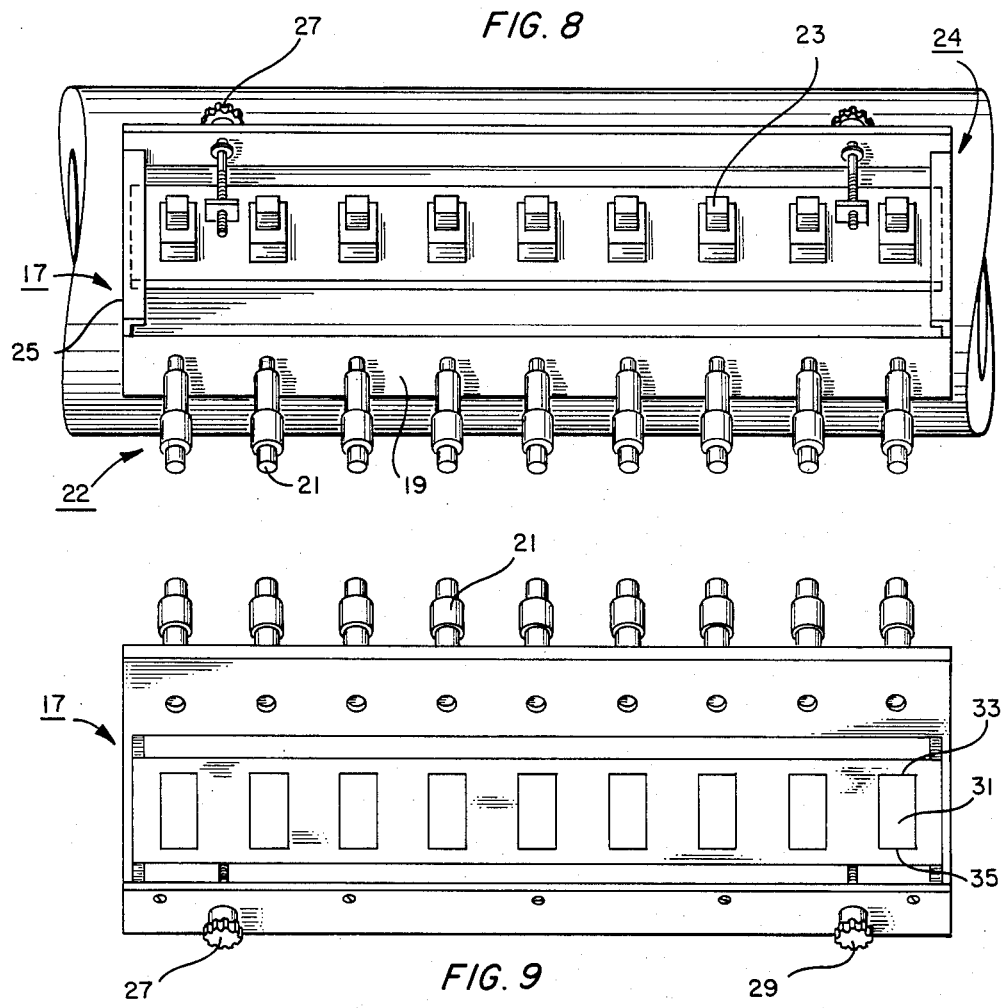
FIG. 8
FIG. 9

ULTRASONIC INSPECTION APPARATUS AND METHOD FOR LOCATING MULTIPLE DEFECTS IN ECCENTRIC WALL TUBULAR GOODS

BACKGROUND OF THE INVENTION

1. Field of the Invention

The present invention relates generally to the art of accoustical defect detection and specifically to an ultrasonic inspection apparatus and method for locating defects in eccentric wall tubular goods, such as oil and gas country pipe.

2. Description of the Prior Art

Ultrasonic transducers are known which have been used in pulse-echo mode to locate flaws and defects in tubular goods. In the pulse-echo mode, the ultrasonic transducer emits an ultrasonic wave and then waits to receive an echo from a defect. The angle of incidence and angle of reflection relative to the surface of the defect must be approximately equal. As a result, a transmitting transducer can only receive an echo from a defect surface which is approximately normal to the direction of ultrasonic wave transmission. If the defect surface is more than about five degrees off-normal to the direction of propagation, the ultrasonic wave will be reflected but will not return a sufficiently large component to the transmitting transducer for the defect to be detected.

Ultrasonic transducers have also been used in the past in pulse-echo mode to generate ultrasonic shear waves which travel peripherally around the tubular goods being examined, and to detect echoes reflected peripherally back to the transducer. Axially oriented ultrasonic transducers have also been used to generate axial shear waves and to detect axial echoes. For some purposes, ultrasonic transducers have been oriented perpendicular to the examined surface, for instance to determine wall thickness, and have been operated in a pulse-echo mode.

A three dimensional defect commonly has at least some surface portion which is normal to one of the pulse-echo operated transducers, so that the defect can be detected. However, a two dimensional defect, such as a crack, can only be detected by pulse-echo transducers which are oriented substantially perpendicular to the surface of the crack. As a result, peripherally oriented pulse-echo transducers and axially oriented pulse-echo transducers are only able to detect cracks which are substantially parallel or perpendicular to the axes.

Certain of the prior art devices have attempted to provide a wider range of coverage by orienting selected transducers at various angles, e.g. forty-five degrees. However, because the direction of propagation must be within five degrees of normal to a crack to be assured of detection, a wide range of wave propagation directions would be required for assuring that cracks would not go undetected.

Inspection of oil and gas country tubular goods causes particular problems when using ultrasonic devices because the pipe is never perfectly concentric. The American Petroleum Institute (API) has written specifications for the limits on which oil and gas country tubular goods can be eccentric. The specifications define a "nominal" wall based upon a weight per foot for a given size diameter pipe. Thus, for a 7 inch outside diameter pipe of 49.50 pounds per foot, the nominal wall is calculated to be 0.730 inches thick. For a 7 inch outside diameter pipe of 66.50 pounds per foot weight, the nominal wall is calculated to be 0.980 inches. The API specifications basically allow the nominal wall to be reduced by only $12\frac{1}{2}\%$ of nominal before being rejected. The same specifications provide that the outside-diameter may not exceed $\frac{3}{4}$ of 1% of the specified outside diameter. In addition, the inside diameter of the pipe must drift, or pass a drift mandrel, of a specific size. For 7 inch pipe of 49.50 pounds per foot weight, this drift diameter is 5.415 inches. From these figures, an allowable wall thickness can be calculated. For instance, for 7 inch pipe of 49.50 pounds per foot weight, the allowable wall can range from about 0.638 inches to 0.818 inches.

In order to overcome shortcomings of the pulse-echo technique, certain prior devices used "thru-transmission" sometimes referred to as pitch-catch techniques. In this technique, a sender element is triggered to transmit an ultrasonic shear wave which is "caught" by a receiver element. The method was generally limited to materials having sufficiently small changes in wall tolerance to allow the receiver transducer to be large enough to catch the incoming ultrasonic signal. Since the prior art devices usually used "point focus" transducers, this method was limited to thin wall tubular goods.

The present invention has as its object a device and method for overcoming the above referenced problems and for providing an ultrasonic inspection system which detects defects and cracks oriented at a wide variety of orientations in the object being examined.

Another object of the invention is to provide an apparatus with a receiving element having a receiving surface which is linear over a larger area than prior devices to receive the incoming signal from the sending element from eccentric wall pipe which varies by the limits specified by API and yet be able to locate defects without false alarms caused by large changes in wall thickness.

SUMMARY OF THE INVENTION

The ultrasonic inspection apparatus of the invention includes a plurality of ultrasonic transducers which are arranged in mated pairs, each of the mated pairs comprising a sender element for transmitting an ultrasonic shear wave which travels in a first direction along the tubular goods being examined, and a receiver element for receiving a reflected ultrasonic wave component from the tubular goods and for transforming it into an electrical signal. Each sender element is a point focus transducer having sufficiently high resolution to maintain detectability of defects in the tubular goods. Each receiver element is a wide focal width transducer having a generally rectangular receiving surface which defines a leading and a trailing edge of the transducer receiving surface. Each receiver element is oriented with respect to each sender element to define an incoming angle for the reflected wave components received by the receiver element. The incoming angle is selected so that for a given outside diameter tubular goods, the thinnest and thickest acceptable wall thicknesses produce reflected wave components which fall within the leading and trailing edges, respectively, of the receiving surface, to compensate for eccentricity in the wall of the tubular goods. An amplitude detecting means determines a drop in relative amplitude of the electrical signal coming from the receiver element below a predetermined threshold and generates a defect output indicative of a defect in the tubular goods being examined.

Additional objects, features and advantages will be apparent in the written description.

BRIEF DESCRIPTION OF THE DRAWINGS

FIG. 7 shows a prior art arrangement of point focus sender and receiver elements, with the elements in place upon pipe which is within acceptable limits of wall thickness.

FIG. 8 is a top, perspective view of a fixture for mounting the sender and receiver elements used in the method of the invention.

FIG. 9 is a bottom view of the fixture of FIG. 8.

DETAILED DESCRIPTION OF THE INVENTION

Figure 1:
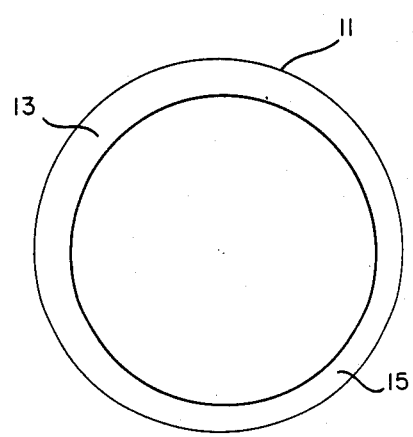
FIG. 1 is a side, cross-sectional view of a tubular good of the type examined by the apparatus of the invention showing the eccentric wall of the tubular good.

FIG. 1 is a cross-sectional view of a cylindrical steel pipe or tube 11 of the type to be examined by the apparatus of the invention. The pipe 11 can be oil and gas country tubular goods such as drill pipe, casing, tubing, and the like. It will be noted that the pipe 11 is "eccentric" having a region of greater wall thickness 13 and a region of lesser wall thickness 15.

FIG. 8 is a top perspective view of an apparatus 17 for a fixture which is used to house the ultrasonic transducers used in inspecting the pipe 11. In practice, it will be understood by those skilled in the art, that the apparatus 17 is arranged over the pipe 11 (shown in dotted lines in FIG. 8) to propagate ultrasonic waves through a coupling medium, such as water, in a collar (not shown) to the examined pipe. The apparatus 17 includes a metal fixture 19 having a first array 21 of "point-focus" ultrasonic transducers 22. The transducers in array 21 are commercially available from a number of sources, e.g., KBI Aerotech of Lewiston, Pa., as "one-half inch round" transducers. Such commercially available point-focus transducers are characterized by an effective beam width at 2 dB of about 0.250 inches×0.250 inches, and have an effective focal distance in water of about 11.0 inches.

Figure 2:
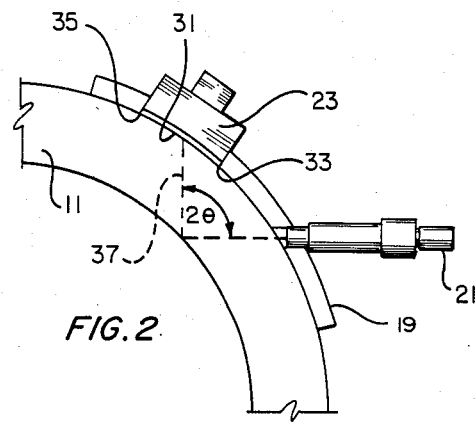
FIG. 2 is a simplified, schematic side view of the sender and receiver elements of the invention showing the elements on a pipe of nominal thickness.

As shown in FIG. 2, the point-focus transducers 21 in array 22 constitute sender elements which are arranged to propagate an ultrasonic shear wave which is propagated circumferentially around the examined pipe 11. The ultrasonic wave is received by a receiver element 23 in a second array 24 which is also retained within the fixture 19. The receiver elements 23 are retained in a sliding tray or carriage 25 which can be adjusted by nuts 27, 29 in order to vary the circumferential distance of the receiver elements 23 from the sender elements 21.

Each of the receiver transducers in the array 24 makes up one element in a mated pair with its corresponding sender element in array 22 for receiving a reflected ultrasonic wave component from the tubular goods and for transforming it into an electrical signal. Each pair of mated transducers forms an arcuate segment extending radially about the tubular goods. Whereas the point-focus transducers in array 22 are selected to have a sufficiently high resolution to maintain detectability of defects in the tubular goods, each receiver element in array 24 is a wide focal width transducer, sometimes referred to as a "paint brush transducer." Such transducers are commercially available from a number of sources including Harisonic Laboratories, Inc., of Stanford, Conn., and from Reference Standard, Inc., of Houston, Tex. The wide focal width transducer in array 24 is selected to have a large effective beam width area to compensate for eccentricity in the wall of the tubular goods being examined. The effective beam width area of each receiver element 23 is at least about 0.750 inches×0.250 and preferably is at least about 1.00 inches×0.250 inches. The effective focal distance in water is approximately 1.50 inches. In addition, the receiver elements must have receiving surfaces which are essentially linear over their entire area so that the response of the receiver elements 23 does not vary more than about 2 dB across the receiving face of the element.

As shown in FIG. 9, each of the receiver elements has a generally rectangular receiving surface 31 which defines a leading and trailing edge 33, 35, respectively, for the transducer. As best seen in FIG. 2, each receiver element 23 is oriented with respect to each sender element 21 to define an incoming angle, denoted "2Θ" in FIG. 2, for the reflective wave components received by the receiver element 23. The calculation of the angle 2Θ will be explained in greater detail later. The incoming angle is selected so that for a given outside diameter tubular goods, the thinnest and thickest acceptable wall thicknesses which are within API standards, produce reflective wave components which fall within the leading and trailing edges 33, 35 of the receiver elements to compensate for eccentricity in the wall of the tubular goods. The incoming angle can be varied by adjusting the position of the receiver array 24 by moving the carriage 25.

FIG. 2 is a simplified illustration of the operation of the sender and receiver elements 21,23 when a pipe of nominal thickness is encountered. The incoming wave component 37 strikes the receiving surface 31 approximately midway between the leading and trailing edges 33, 35. The relative position of the sender and receiver elements 21,23 has been pre-set at start up so that the incoming wave component 37 strikes the leading edge of the receiver element 23 for a pipe which has a thin wall, but which is still within accepted API standards.

Figure 3:
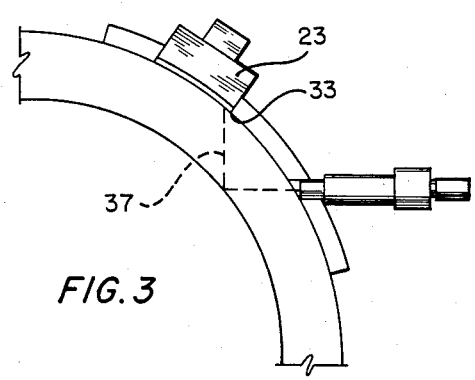
FIG. 3 is similar to FIG. 2 showing the sender and receiver elements on a thin wall pipe which is within acceptable limits.
Figure 4:
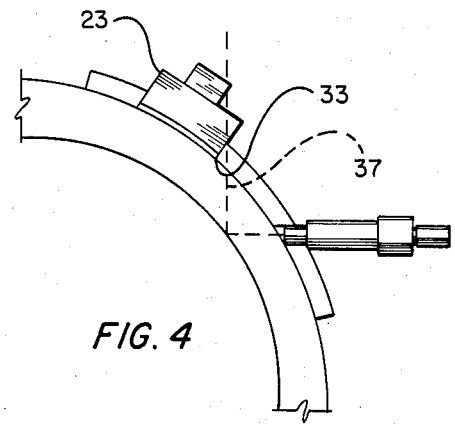
FIG. 4 is similar to FIG. 2 and shows the sender and receiver elements on a pipe which is thinner than acceptable limits.
Figure 5:
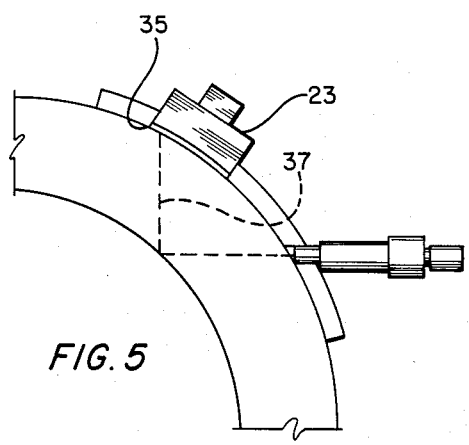
FIG. 5 is similar to FIG. 2 and shows the sender and receiver elements on a thick wall pipe which is within acceptable limits.

FIG. 4 illustrates the incoming wave component 37 missing the leading edge 33 for a pipe with a wall thickness which is thinner than acceptable standards. FIG. 5 illustrates the opposite case from FIG. 3 in which the incoming wave component 37 strikes the trailing edge 35 of the receiver element 23, where the pipe wall is thicker than nominal but still within accepted API standards. As has been discussed, for 7 inch wall pipe, the allowable wall thickness can vary between about 0.638 and 0.818 inches. A one inch by ¼ inch "paint brush" receiver element which is linear in response over substantially the entire receiving surface has been found to be adequate to accommodate the entire range of oil and gas country tubular goods normally encountered.

Figure 6:
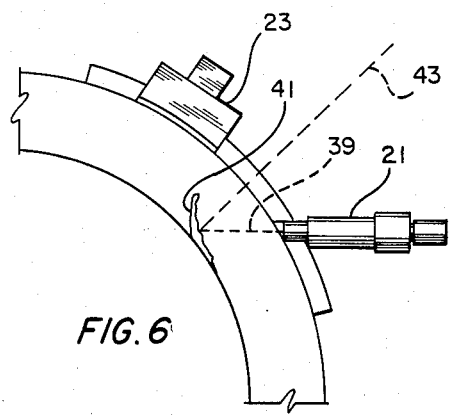
FIG. 6 is similar to FIG. 2 and shows the sender element striking a defect within the tubular goods.

FIG. 6 illustrates the ultrasonic pulse 39 emitted by the sender element 21 striking an oblique defect 41 in the pipe wall, causing the reflected wave component 43 to go off at an angle and to miss the receiver element 23. The absence of a return signal at the receiver element 23 causes a defect indication in the system electronics.

Figure 11:
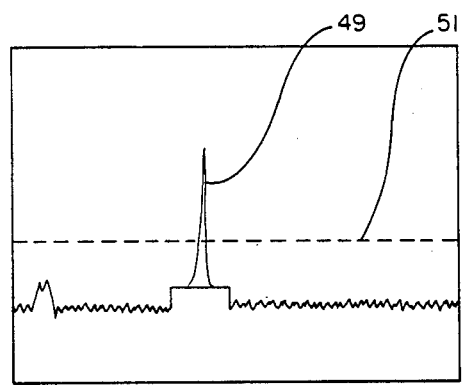
FIG. 11 is a simplified, schematic view showing a readout of the amplitude detecting means of the invention.
Figure 12:
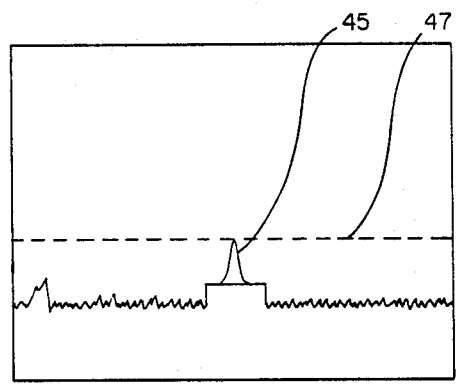
FIG. 12 is similar to FIG. 11 and shows a readout of a defect indication from the amplitude detecting means.

The sender and receiver elements in the arrays 22, 24 are controlled by a commercially available multiplexing means (not shown) which switches triggering pulses to selected ultrasonic transducers. The multiplexing means is operated to selectively turn mated pairs of sender and receiver elements on and off. Such multiplexing devices are known to those skilled in the art. An amplitude detecting means, the output of which is illustrated graphically in FIGS. 11 and 12, determines a drop in relative amplitude of the electrical signal coming from the receiver element below a predetermined threshold and generates a defect output indicative of a defect in the tubular goods in the conditions represented by FIGS. 4 and 6. The amplitude detecting means illustrates this condition graphically in FIG. 12 where the electrical signal 45 falls below a predetermined threshold 47. Where the pipe is within API standard for wall thickness and no defect is present (FIGS. 2, 3 and 5) the amplitude output appears as in FIG. 11 with an electrical signal 49 which is over the predetermined threshold 51. The preferred defect detecting means, illustrated graphically in FIGS. 11 and 12, is sometimes referred to as a "negative gate" and results in a positive voltage being detected where no defect is present and a drop in voltage or loss of signal where the pipe is outside wall thickness standards or where a defect is present. Such amplitude detecting means are commercially available from a number of sources such as the ECHOGRAPH 1054 manufactured by Karl Deutsh of Wuppertal, West Germany.

Figure 10:
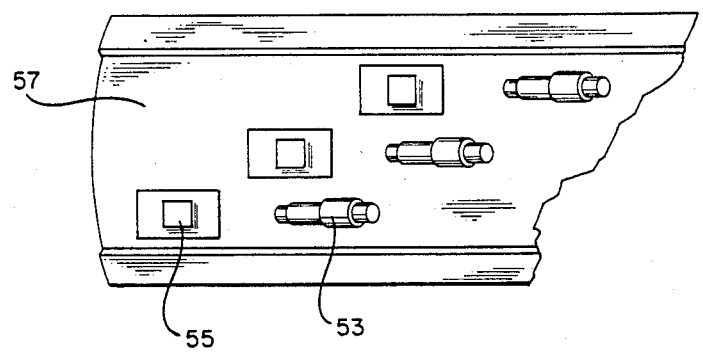
FIG. 10 is a top, partial view of a fixture similar to FIG. 8 showing another arrangement of the sender and receiver elements of the invention.

Although the sender and receiver elements 21, 23 have been illustrated as being arranged to propagate waves circumferentially about the pipe 11, it will be understood by those skilled in the art that other arrangements are possible to provide full 360° inspection of the tubular goods. In FIG. 10, the sender elements 53 and receiver elements 55 are arranged in a fixture 57 so that when the fixture is arranged over the longitudinal axis of the pipe 11, the sender elements 53 are oriented to transmit ultrasonic shear waves which propagate axially along the tubular goods. The arrangements shown in FIGS. 8-10 are particularly effective for locating multiple oblique defects in eccentric wall tubular goods. It will be understood by those skilled in the art that the techniques are also readily adaptable for use in combination with traditional wall thickness and longitudinal defect detecting devices, such as those using point focus transducers in pulse-echo mode. The tubular goods being inspected can also be rotated while moving axially past the mated transducers to generate a helical inspection pattern and further saturate the pipe wall.

Figure 13:
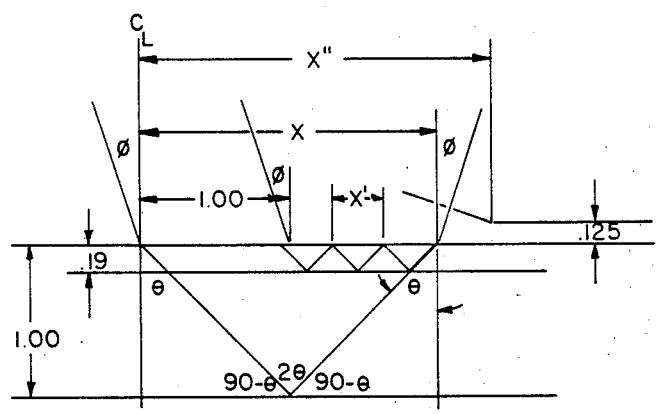
FIG. 13 is a diagram illustrating the calculation of the angle between the sender and receiver elements.

The ability of the mated pairs of transducers to be used with a negative gate amplitude detecting means to test eccentric pipe is dependent upon the response amplitude of the receiver "paint brush" transducers being linear along the entire length of the receiving surface 31, and the orientation of the sender and receiver elements. As has been discussed, the orientation of the sender and receiver elements 21,23 can be pre-set at start up for a given pipe size to locate multiple oblique defects within the pipe wall, without giving false alarms for pipe walls which are eccentric but continue to fall within acceptable standards. FIG. 13 illustrates a method of calculating the orientation parameters of the sender and receiver elements in the fixture 19, including multiple skips (N) of the reflected shear wave components of the ultrasonic wave.

Given: Max wall=1.00", min. wall=0.19", receiver length=1.00" and water path=0.125".

Find: N=# of skips in min. wall to reach receiver at the same refracted angle ($\Theta$) it takes 1 skips in max wall.

$\Theta$=refracted angle in steel.

x−1=distance between receiver element leading edge and the sender element center line on steel.

$\phi$=incident angle in water.

x″=distance between receiver element center line and sender element trailing edge on fixture.

$$\phi = \tan^{-1}\left(\frac{.058^4}{.13} \sin \Theta\right)$$

FORMULAS $$x' = 2 \text{ (min. wall) Tan}\Theta = \frac{x-1}{N}$$

$$x' = 0.38 \text{ Tan } \Theta$$

$$x - 1 = 0.38 \, N \text{ Tan } \Theta$$

$$N = \frac{1}{2 \text{ (min. wall)}} (2 \text{ max. wall} - \text{Cot}\Theta)$$

$$N = \frac{1}{.38} (2 - \text{Cot}\Theta)$$

$$\Theta = \text{Tan}^{-1} 1/(2 \text{ max. wall} - (2 \text{ min. wall } N))$$

$$\Theta = \text{Tan}^{-1} 1/(2 - 0.38N)$$

$$x'' = (x - 1) + \frac{\text{rec. dim.}}{2} + \frac{x' \text{mtr. dia.}}{2} \text{ Sec. } \phi$$

$$x'' = (x-1) + \tfrac{1}{2} + \tfrac{1}{4} \text{ Tan } \phi + 0.315 \text{ Sec. } \phi$$

| N | $\Theta$ | x − 1 | $\phi$ | x″ |
|---|---|---|---|---|
| 1 | 31.7 | .235 | 13.7 | 1.12 |
| 2 | 38.9 | .613 | 16.4 | 1.52 |
| 3 | 49.3 | 1.33 | 19.9 | 2.26 |
| 4 | 64.4 | 3.17 | 23.9 | 4.125 |
| 5 | 84.3 | 19.04 | 26.6 | 20.02 |
| 6 | >90 | δ | ≧26.7 | δ |
| 2.63 | 45 | 1.00 | 18.5 | 1.92 |

FIG. 7 illustrates the prior art arrangement of sender elements 59 and receiver elements 61, which are both typically point-focus transducers having effective beam widths which were much smaller (typically about 0.250 inches×0.250 inches) than the receiver elements 23 in applicants' invention. As shown in FIG. 7, a piece of eccentric wall pipe could be within standard and yet the reflected wave component 63 would not be detected by the receiver element 61, causing a false alarm to be detected.

In the method of Applicants' invention, a plurality of ultrasonic transducers are arranged in mated pairs about the tubular goods to be inspected. Each mated pair has a sender element for transmitting an ultrasonic shear wave which travels in a first direction along the tubular goods being examined. The mated pairs also include receiver elements for receiving ultrasonic wave components from the tubular goods and for transforming it into an electrical signal.

The receiver elements are provided as wide focal width transducers having generally rectangular receiving surfaces which define leading and trailing edges for each receiver transducer. Each receiver element is oriented with respect to each sender element to define an incoming angle for the reflected wave component received by the receiver element.

For a given outside diameter tubular good, the reflective angle produced by the thinnest and thickest walls which are acceptable under the testing standard is determined. The orientation of the receiver elements relative to the sender elements is then adjusted so that the wall components from the thinnest and thickest walls which are acceptable continue to be received by the receiver elements. The system is then operated to detect a drop in relative amplitude of the electrical coming from the receiver elements below a predetermined threshold and to generate a defect output indicative of a defect in the tubular goods being examined.

An invention has been provided with several advantages. The ultrasonic inspection apparatus of the invention is not highly orientation dependent as were prior pulse-echo systems. The method used with the apparatus of the invention utilizes a negative gate applitude detecting means which only emits an alarm when no return signal is detected. Because a through-transmission mode is utilized between the sender and receiver elements, a larger angle of inspection can be achieved than with prior art pulse-echo devices which only located defects within about five degrees of normal. Because only one sender and receiver pair need be triggered at one time, the multiplexing electronics is simpler than in prior art devices.

While the invention has been shown in only one of its form, it is not thus limited but is susceptible to various changes and modifications without departing from the spirit thereof.

We claim:

1. An ultrasonic inspection apparatus for locating multiple defects in eccentric wall tubular goods, comprising:

a plurality of ultrasonic transducers arranged in mated pairs, each of the mated pairs comprising a sender element for transmitting an ultrasonic shear wave which travels in a first direction along the tubular goods being examined, and a receiver element for receiving a reflected ultrasonic wave component from the tubular goods and for transforming it into an electrical signal; and wherein each sender element is a point focus transducer having sufficiently high resolution to maintain detectability of defects in the tubular goods and wherein each receiver element is a wide focal width transducer having a large effective beam width area to compensate for eccentricity in the wall of the tubular goods.

2. The apparatus of claim 1, wherein the sender elements are oriented to transmit ultrasonic shear waves which propagate circumferentially around the tubular goods.

3. The apparatus of claim 1, wherein the sender elements are oriented to transmit ultrasonic shear waves which propagate axially along the tubular goods.

4. The apparatus of claim 1, wherein the effective beam width area of each receiver element is at least 1.0 inches×0.250 inches and wherein the response amplitude of the receiver elements does not vary more than 2 db over the effective beam width area.

5. An ultrasonic inspection apparatus for locating multiple defects in eccentric wall tubular goods, comprising:

a plurality of ultrasonic transducers arranged in mated pairs, each of the mated pairs comprising a sender element for transmitting an ultrasonic shear wave which travels in a first direction along the tubular goods being examined, and a receiver element for receiver a reflected ultrasonic wave component from the tubular goods and for transforming it into an electrical signal; and wherein each sender element is a point focus transducer having sufficiently high resolution to maintain detectability of defects in the tubular goods and wherein each receiver element is a wide focal width transducer having a generally rectangular receiving surface which defines a leading and a trailing edge of the transducer, each receiver element being oriented with respect to each sender element to define an incoming angle for the reflected wave components received by the receiver element, the incoming angle being selected so that for a given outside diameter tubular goods the thinnest and thickest acceptable wall thicknesses produce reflected wave components which fall within the leading and trailing edges, respectively, of the receiving surface to compensate for eccentricity in the wall of the tubular goods.

6. An ultrasonic inspection apparatus for locating multiple defects in eccentric wall tubular goods, comprising:

a plurality of ultrasonic transducers arranged in mated pairs, each of the mated pairs comprising a sender element for transmitting an ultrasonic shear wave which travels in a first direction along the tubular goods being examined, and a receiver element for receiver a reflected ultrasonic wave component from the tubular goods and for transforming it into an electrical signal;

wherein each sender element is a point focus transducer having sufficiently high resolution to maintain detectability of defects in the tubular goods and wherein each receiver element is a wide focal width transducer having a generally rectangular receiving surface which defines a leading and a trailing edge of the transducer, each receiver element being oriented with respect to each sender element to define an incoming angle for the reflected wave components received by the receiver element, the incoming angle being selected so that for a given outside diameter tubular goods the thinnest and thickest acceptable wall thicknesses produce reflected wave components which fall within the leading and trailing edges, respectively, of the receiving surface to compensate for eccentricity in the wall of the tubular goods; and amplitude detecting means for determining a drop in relative amplitude of the electrical signal coming from the receiver element below a predetermined threshold and for generating an defect output indicative of a defect in the tubular goods being examined.

7. An ultrasonic testing method for locating multiple defects in eccentric wall tubular goods which would cause the goods to be outside a given testing standard, comprising the steps of:

arranging a plurality of ultrasonic transducers as mated pairs about the tubular goods to be inspected, each mated pair having a sender element for transmitting an ultrasonic shear wave which travels in a first direction along the tubular goods being examined, and having a receiver element for receiver a reflected ultrasonic wave component from the tubular goods and for transforming it into an electrical signal;

providing the receiver elements as wide focal width transducers having generally rectangular receiving surfaces which define leading and trailing edges for each receiver transducer;

orienting each receiver element with respect to each sender element to define an incoming angle for the reflected wave component received by the receiver element;

determining for a given outside diameter tubular good the reflective angle produced by the thinnest and thickest walls which are acceptable under the testing standard;

adjusting the orientation of the receiver elements relative to the sender elements so that the wave components from the thinnest and thickest walls which are acceptable continue to be received by the receiver elements; and detecting a drop in relative amplitude of the electrical signal coming from the receiver element below a predetermined threshold and generating a defect output indicative of a defect in the tubular goods being examined.

8. The method of claim 7, further comprising the steps of arranging a plurality of mated pairs of transducers which are oriented to transmit ultrasonic shear waves which propagate circumferentially around the tubular good; and rotating the tubular goods while moving the tubular goods axially past the mated transducers to generate a helical inspection pattern.

9. The method of claim 8, wherein each pair of mated transducers forms an arcuate segment extending radially about the tubular goods.

10. The method of claim 7, further comprising the steps of arranging a plurality of mated transducers which are oriented to transmit ultrasonic shear waves which propagate axially along the tubular goods, each pair of mated transducers being aligned axially along the longitudinal axis of the tubular goods and being staggered radially from the next adjacent pair of mated transducers.

* * * * *